United States Patent [19] … [11] 4,322,349
Annen et al. … [45] Mar. 30, 1982

[54] PROCESS FOR PREPARING 6-METHYLENE STEROIDS

[75] Inventors: Klaus Annen; Henry Laurent; Helmut Hofmeister; Rudolf Wiechert, all of Berlin, Fed. Rep. of Germany

[73] Assignee: Schering Aktiengesellschaft, Berlin, Fed. Rep. of Germany

[21] Appl. No.: 235,240

[22] Filed: Feb. 17, 1981

Related U.S. Application Data

[63] Continuation-in-part of Ser. No. 231,715, Feb. 5, 1981, abandoned.

[30] Foreign Application Priority Data

Feb. 5, 1980 [DE] Fed. Rep. of Germany ....... 3004508

[51] Int. Cl.³ .............................................. C07J 5/00
[52] U.S. Cl. ................. 260/239.55 R; 260/239.55 D; 260/397.1; 260/397.3; 260/397.4; 260/397.45; 260/397.47; 260/239.57
[58] Field of Search ............ 260/239.55 R, 239.55 C, 260/397.1, 397.3, 397.4, 397.45, 397.47

[56] References Cited

U.S. PATENT DOCUMENTS 3,095,411  6/1963  Keik et al. .................... 260/397.45
3,328,433  6/1967  Cooley et al. ................. 260/397.45
3,389,154  6/1968  Burh et al. ................... 260/397.45

Primary Examiner—Elbert L. Roberts
Attorney, Agent, or Firm—Millen & White

[57] ABSTRACT

A process for preparing a 6-methylene-$\Delta^4$-3-keto steroid of the formula

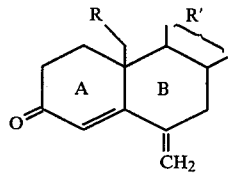

wherein
R is hydrogen, alkoxy of up to 6 carbon atoms or acyloxy of up to 6 carbon atoms wherein the acyl group is that of a carboxylic acid, and
R' is the CD-ring system of a steroid of the androstane or pregnane series,
comprising reacting the corresponding $\Delta^4$-3-keto steroid of the formula

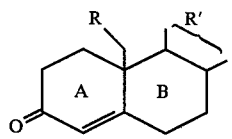

with a formaldehyde derivative of the formula

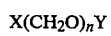

wherein
n is 1, 3 or an integer on the order of 100–1000, and
X is $C_{1-5}$ alkoxy and Y is $C_{1-5}$ alkyl when n is 1,
X and Y represent a single bond between the terminal C atom and the terminal O atom when n is 3, and
X is hydroxy and Y is hydrogen when n is an integer on the order of 100–1000,
in an inert solvent in the presence of a condensation agent which is a strong acid a strongly acidic cation exchanger or a phosphoric acid derivative.

13 Claims, No Drawings

PROCESS FOR PREPARING 6-METHYLENE STEROIDS

CROSS REFERENCE TO RELATED APPLICATION

This application is a continuation in part application of U.S. application Ser. No. 231,715, filed on Feb. 5, 1981, of the same title and inventive entity now abandoned.

BACKGROUND OF THE INVENTION

The present invention relates to a process for preparing 6-methylene steroids.

Adding a methyl group in the 6-position of steroids frequently evokes a considerable increase in activity, notably for progestogens and corticoids. Thus, many efforts have been made in the past to provide methods for introducing such methyl groups into the 6-position with maximum simplicity, e.g., via added 6-methylene groups. Unfortunately, the conventional methods for introducing 6-methylene groups in steroids are all very expensive and require several stages.

SUMMARY OF THE INVENTION

Accordingly, it is an object of the present invention to provide a process for introducing a methylene group in a simple way into the 6-position of steroids, thus forming a desirable starting material for the preparation of 6-methyl steroids.

Upon further study of the specification and appended claims, further objects and advantages of this invention will become apparent to those skilled in the art.

These objects have been attained by providing a process for preparing 6-methylene-$\Delta^4$-3-keto steroids of the partial formula I

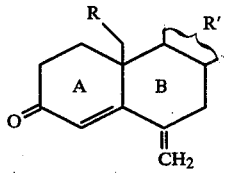

(I)

wherein
R is hydrogen, acyloxy or alkoxy of up to 6 carbon atoms and
R' is the CD-ring skeleton of steroids of the androstane and pregnane series,
comprising treating $\Delta^4$-3-keto steroids of the partial formula II

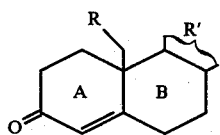

(II)

wherein R and R' are as defined above, in an inert solvent, with a condensation agent at a temperature of 0°–80° C. with a formaldehyde derivative of the formula

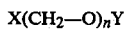

X(CH$_2$—O)$_n$Y wherein

X is alkoxy and Y is alkyl, each of up to 5 carbon atoms when n=1, or
X and Y represent a C-O single bond when n=3, or
X is hydroxy and Y is hydrogen when n is an integer on the order of 100–1000.

DETAILED DISCUSSION

The success of the reaction of this invention is surprising since a direct condensation of $\Delta^4$-3-keto steroids with formaldehyde or the described formaldehyde derivatives to obtain the corresponding 6-methylene-$\Delta^4$-3-keto steroids was not foreseeable to one skilled in the art.

The process of this invention has the advantage that it requires fewer stages than conventional methods for introducing a methylene or methyl group into the 6-position of 3-keto-$\Delta^4$-steroids. For example, 3,5-dienol ether formation, as described, for example, by Petrow et al., Tetrahedron 21 : 1624 (1965), and 3,5-dienamine formation of the 3-keto-$\Delta^4$-system prior to electrophilic CC-linkage on the C-6 carbon atom, as disclosed, for example, by Fürst et al., Helv. Chim. Acta 56 : 2396 (1973), are unnecessary. Also, there is no need to block the 3-keto group before a 5α,6α-epoxy ring opening reaction with Grignard reagents as disclosed, for example, by Spero et al., J. Amer. Chem. Soc. 78 : 6213 (1956).

An advantage of the process of this invention, thus, is that a $\Delta^4$-3-keto steroid directly yields, in a single step, a $\Delta^4$-3-keto-6-methylene steroid. The latter, if desired, can then be conventionally hydrogenated to known $\Delta^4$-3-keto-6α-methyl steroids or isomerized to known $\Delta^{4,6}$-3-keto-6-methyl steroids.

The unshown partial segment of the CD-ring skeleton of the steroids can be conventionally substituted. The structure of this segment is not critical to the successful performance of the process of this invention since it has no effect on the course thereof. The D-ring can be 5-membered (cyclopentanophenanthrene series) or 6-membered (D-homo series). The CD-rings can be structured and substituted as shown, for example, in the following formulae:

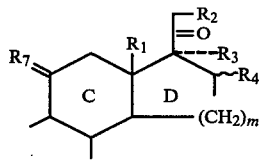

wherein
m=1 or 2,
R$_1$ is methyl or ethyl,
R$_2$ is hydrogen, acyloxy of up to 12 carbon atoms, halogen, such as fluorine, chlorine or bromine, alkoxy of up to 6 carbon atoms, or an acetal group of the formula

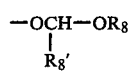

wherein
R'$_8$ is hydrogen or alkyl of up to 6 carbon atoms and
R$_8$ is alkyl of up to 6 carbon atoms, $R_3$ is hydrogen, hydroxy or alkyl, alkoxy or acyloxy, each of up to 6 carbon atoms, nitrooxy, or an acetal or hemithioacetal group of the formula $$-\underset{\underset{R_8'}{|}}{O}CH-ZR_8$$

wherein $R'_8$ and $R_8$ are as defined above, and Z is oxygen or sulfur, $R_4$ is hydrogen, α- or β-alkyl, alkylidene, α- or β-acyloxy, α- or β-alkoxy, each of up to 6 carbon atoms and α- or β-$OCH_2OR_8$ wherein $R_8$ is as defined above, or $R_3$ and $R_4$ together represent oxygen, methylene, or the group $$\begin{array}{c}-O\diagdown\quad R_9\\ \phantom{-O}C\\ -O\diagup\quad R_{10}\end{array}$$

wherein $R_9$ and $R_{10}$ can be identical or different and each is hydrogen, alkyl, or alkoxy, each of up to 6 carbon atoms, and $R_7$ is oxygen; or hydrogen and trimethylsilyl, β-hydroxy, nitrooxy, β-halogen such as fluorine or chlorine, lower α- or β- acyloxy, lower α- or β-alkoxy, each of up to 6 carbon atoms, α- or β-methoxymethoxy; or methylene; or

[structure with rings C, D, $R_1$, $R_7$, and dioxolane groups]

wherein $R_1$ and $R_7$ are as defined above; or

[structure with rings C, D, $R_1$, $R_2$=O, $R_4$, $(CH_2)_m$]

wherein m, $R_1$, $R_2$ and $R_4$ are as defined above, and $C_9\text{---}C_{11}$ is a CC single or double bond; or

[structure with rings C, D, $R_1$, $R_{12}$]

wherein $R_1$ is as defined above and $R_{12}$ is oxygen, ethylene dioxy, or $=C-COOR_8$ wherein $R_8$ is as defined above; or

[structure with rings C, D, $R_1$, lactone]

wherein $R_1$ is as defined above; or

[structure with rings C, D, $R_1$, $COOR_5$, $R_3$]

wherein $R_1$ and $R_3$ are as defined above and $R_5$ is alkyl or haloalkyl, each of up to 6 carbon atoms; or

[structure with rings C, D, $R_1$, $R_6$, $R_{11}$]

wherein $R_1$ is as defined above and $R_6$ is hydroxy, acyloxy of up to 6 carbon atoms, nitrooxy, alkoxy of up to 6 carbon atoms, or the acetal or hemithioacetal group of the formula $$-\underset{\underset{R_8'}{|}}{O}CH-ZR_8$$

wherein $R_8$, $R'_8$ and Z are as defined above, and $R_{11}$ is alkyl, alkenyl or alkynyl, each of up to 6 carbon atoms, which can optionally be substituted by fluorine, chlorine or bromine, or

[structure with rings C, D, $R_1$, $R_2$=O, O, $CH_2$]

wherein $R_1$ and $R_2$ are as defined above.

Throughout this discussion, acyloxy of up to 6 or 12 carbon atoms is understood to include acid residues derived from acids customarily employed for esterifications in steroid chemistry. Preferred acids are hydrocarbon carboxylic acids of 1–12 carbon atoms. The carboxylic acids can also be unsaturated, branched, polybasic, or substituted in the usual way, for example by hydroxy, amino, oxo groups, or halogen atoms. These include cycloaliphatic, aromatic, mixed aromatic-aliphatic, or heterocyclic acids which can likewise be substituted as usual, for example by halogen atoms. All of these acids in this sense are equivalents for use in the process components. Preferred acids for forming the acyl residues are, for example: acetic acid, propionic acid, caproic acid, enanthic acid, undecylic acid, oleic acid, trimethylacetic acid, trifluoroacetic acid, dichloroacetic acid, cyclopentylpropionic acid, cyclohexylacetic acid, phenylpropionic acid, phenylacetic acid, phenoxyacetic acid, dialkylaminoacetic acid, piperidinoacetic acid, succinic acid, benzoic acid, and others.

Lower acyloxy of up to 6 carbon atoms is understood to mean acid residues derived from lower such carboxylic acids. Examples include formic acid, acetic acid, propionic acid, butyric acid, and caproic acid.

Lower alkyl or alkoxy groups of up to 6 carbon atoms are understood to include residues derived from the corresponding aliphatic hydrocarbons, such as, for example, methane, ethane, propane, isopropane, n-butane, isobutane, and tert-butane.

n can be 1, 3 an integer on or the order of 100–1000. When n is 1, X is $C_{1-5}$ alkoxy and Y is $C_{1-5}$ alkyl. When n is 3, X and Y represent a single bond between the terminal C atom and the terminal O atom, thereby forming a trioxane group. When n is on the order of 100–1000, X is hydroxy and Y is hydrogen.

In general, any formaldehyde derivative would be suitable for use in the process of this invention as long as it affords formaldehyde under the reaction conditions.

The process of this invention is conducted in an inert solvent. Examples include methylene chloride, chloroform, carbon tetrachloride, 1,2-dichloroethane, diethyl ether, dioxane, tetrahydrofuran and petroleum ether. Such solvents can also be used in mixtures with one another.

Suitable condensation agents actually include all phosphoric acid derivatives, such as phosphorus pentoxide, phosphorus oxychloride, phosphorus oxytribromide, ethyl dichlorophosphite, diethyl chlorophosphite, phosphorus pentachloride, etc.

Preferred phosphoric acid derivatives can be formulated as satisfying the following formula, $PQ_aQ'_b$, wherein a and b are integers of 0 to 5 and Q and Q' are halogen, oxygen and $C_1$ to $C_2$ alkyl.

Likewise suitable are strong acids, e.g., of a pKa less than 1, such as, concentrated sulfuric acid, hydrochloric acid, p-toluenesulfonic acid, and perchloric acid, as well as strongly acidic cation exchangers based on synthetic resins, such as polystyrene, epoxy resins or polyacrylates, e.g., Amberlyst® (Aldrich & Co., Milwaukee, Wisc.) or Levatit® (E. Merck, Darmstadt, Germany). Such exchangers are discussed, e.g., in Chemical Engineer's Handbook, Perry & Chilton, 5th Ed., McGraw-Hill (1973), Chapter 16, whose disclosure is incorporated by reference herein. Preferred agents which have proven themselves well are phosphorus pentoxide and phosphorus oxychloride.

Reaction temperatures are 0°–150° C.; preferred is 20°–80° C. Typical reaction times are 2–20 hours, preferably 1–6 hours. Generally, 10–1000, preferably 50–150 molar equivalents of the formaldehyde derivative are employed per mole of starting steroid. 0.5–10, preferably 1–2 molar equivalents of the condensation agent are employed per mole of starting steroid. The amount of solvent is not critical; usually, equal amounts are used based on the weight of the formaldehyde derivative. Order of addition of reactants is not critical. Yields generally are at least 50% of the theoretical yield.

Although the reaction of this invention can be carried out in a simple way using the aforementioned condensation agents, it is recommended, when using phosphorus pentoxide, to employ a carrier material to obtain a better distribution of the condensation agent. Suitable carrier materials include, for example, kieselguhr, silica gel, "Celite", aluminum oxide, bleaching clay, bentonites and graphite. When using halophosphoric acid derivatives, the addition of a buffer is advantageous. Suitable buffer substances include alkali salts of weak organic acids, such as, for example, sodium acetate, potassium acetate, and sodium citrate, and salts of phosphoric acid, such as, for example, potassium dihydrogen phosphate and disodium hydrogen phosphate.

The amount of such added carrier material and/or buffer compound is not critical but generally is 500–1000 wt.% and 5–50 wt.%, respectively, based on the weight of the condensation agent.

The 6-methylene steroids producible according to this invention can be used as starting materials for the direct preparation of 6-methyl steroids. These can be obtained according to conventional methods from corresponding 3-keto-$\Delta^4$-6-methylene steroids by isomerization, yielding 3-keto-6-methyl-$\Delta^{4,6}$-steroids (see, e.g., Tetrahedron Letters 21(1965) 1624) or, by hydrogenation with subsequent epimerization by acid treatment of these compounds, yielding 3-keto-6α-methyl-$\Delta^4$-steroids (see, e.g., Tetrahedron Letters 25 (1969) 1155).

For example, the following conventional progestogens and corticoids can be prepared from the corresponding starting material steroids of Formula I above:

Medroxyprogesterone-acetate from 17α-acetoxy-6-methylene-4-pregnene-3,20-dione; 6α-methyl prednisolone from 11β,17α-21-trihydroxy-6-methylene-1,4-pregnadiene-3,20-dione; medroxyprogesterone from 17α-hydroxy-6-methylene-4-pregnene-3,20-dione; mesgestrol acetate from 17α-acetoxy-6-methylene-4,6-pregnadiene-3,20-dione; medrogestone from 17-methyl-6-methylene-4,6-pregnadiene-3,20-dione; etc.

The starting materials of Formula II above are general very well-known, and, when necessary, can be prepared from conventional starting materials using the very many conventional reactions utilized in preparative steroid chemistry.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A solution of 5.0 g of 17,21-diacetoxy-4-pregnene-3,20-dione in 35 ml of anhydrous methylene chloride and 22.5 ml of methylal is combined in incremental portions at room temperature with a mixture of 1.0 g of phosphorus pentoxide and 7.5 g of silica gel. The mixture is agitated for 3 days at room temperature and then another 11 ml of methylal, 500 mg of phosphorus pentoxide, and 3.75 g of silica gel are added. After another 2 days, the reaction mixture is vacuum-filtered, the residue is washed thoroughly with methylene chloride, and evaporated to dryness under vacuum. The crude product is purified on 350 g of silica gel with a hexane/ethyl acetate gradient (0–50% ethyl acetate), thus obtaining 3.6 g of 17α,21-diacetoxy-6-methylene-4- pregnene-3,20-dione, mp 227°–228° C. $[\alpha]_D^{25} = +165°$ (chloroform).

EXAMPLE 2

5.0 g of 17α-acetoxy-4-pregnene-3,20-dione is reacted analogously to Example 1 to 2.7 g of 17α-acetoxy-6-methylene-4-pregnene-3,20-dione, mp 232.5°–234° C.

EXAMPLE 3

2.0 g of 17β-acetoxy-4-androsten-3-one is reacted under the conditions of Example 1 and purified, yielding 860 mg of 17β-acetoxy-6-methylene-4-androsten-3-one, mp 138°–140° C.

EXAMPLE 4

5.0 g of 21-acetoxy-17α-nitrooxy-4-pregnene-3,20-dione is reacted analogously to Example 1 to 2.4 g of 21-acetoxy-6-methylene-17α-nitrooxy-4-pregnene-3,20-dione, mp 136°–137° C.

EXAMPLE 5

Under the conditions of Example 1, 5.0 g of 21-acetoxy-11β,17α-dinitrooxy-4-pregnene-3,20-dione is reacted to 2.6 g of 21-acetoxy-6-methylene-11β,17α-dinitrooxy-4-pregnene-3,20-dione, mp 167.5°–171° C. (decomposition).

EXAMPLE 6

Analogously to Example 1. 5.0 g of 21-acetoxy-4,16-pregnadiene-3,20-dione is reacted to 2.3 g of 21-acetoxy-6-methylene-4,16-pregnadiene-3,20-dione, mp 159.5°–161° C.

EXAMPLE 7

5.0 g of 4-androstene[17(β-1')-spiro-5']perhydrofuran-2',3-dione is reacted and purified under the conditions of Example 1, yielding 2.5 g of 6-methylene-4-androstene[17(β-1')-spiro-5']perhydrofuran-2',3-dione, mp 142°–143° C.

EXAMPLE 8

A mixture of 17α,21-diacetoxy-4-pregnene-3,20-dione and 3,17α,21-triacetoxy-3,5-pregnadien-20-one, prepared from 5.0 g of 21-acetoxy-17α-hydroxy-4-pregnene-3,20-dione in 63 ml of diethylene glycol dimethyl ether with 7.4 g of N,N-dimethylaminopyridine and 7.4 ml of acetic anhydride by 6.5 hours of agitation at 80° C., is reacted under the conditions of Example 1 to 2.4 g of 17α,21-diacetoxy-6-methylene-4-pregnene-3,20-dione, mp 227°–228° C.

EXAMPLE 9

A suspension of 1.0 g of sodium acetate in 30 ml of methylene chloride, 30 ml of formaldehyde dimethylacetal and 3.8 ml of phosphorus oxychloride is combined with 1.0 g of 17,21-diacetoxy-4-pregnene-3,20-dione and refluxed for 35 hours under agitation. After cooling to room temperature, the mixture is diluted with methylene chloride and water. Under stirring, a saturated soda solution is added dropwise until an alkaline reaction of the aqueous phase has been obtained. The organic phase is separated, washed with water, dried over sodium sulfate, and evaporated under vacuum. Finally, the product is recrystallized from acetone/hexane, thus isolating 825 mg of 17,21-diacetoxy-6-methylene-4-pregnene-3,20-dione, mp 227°–228° C.

EXAMPLE 10

Analogously to Example 1, 1.0 g of 19-acetoxy-17-hexanoyloxy-4-pregnene-3,20-dione in 7 ml of methylene chloride is reacted with 4.9 ml of formaldehyde dimethylacetal and a mixture of 200 mg of phosphorus pentoxide and 1.5 g of kieselguhr W 20, and worked up. The crude product is purified on 110 g of silica gel with a hexane/acetone gradient (0–20% acetone), thus isolating 563 mg of 19-acetoxy-17-hexanoyloxy-6-methylene-4-pregnene-3,20-dione, mp 111°–112° C.

EXAMPLE 11

Analogously to Example 9, 2.0 g of 17,21-diacetoxy-4-pregnene-3,20-dione in 60 ml of methylene chloride is reacted with 60 ml of formaldehyde dimethylacetal, 2.0 g of sodium acetate, and 12.6 g of phosphorus oxybromide, and worked up, thus isolating 1.68 g of 17,21-diacetoxy-6-methylene-4-pregnene-3,20-dione, mp 226°–228° C.

EXAMPLE 12

A solution of 2.0 g of 17,21-diacetoxy-4-pregnene-3,20-dione in 60 ml of methylene chloride and 60 ml of formaldehyde dimethylacetal is refluxed for 30 hours with 2.0 g of sodium acetate and 12.6 g of phosphorus pentachloride. The mixture is worked up analogously to Example 9, thus isolating 1.21 g of 17,21-diacetoxy-6-methylene-4-pregnene-3,20-dione, mp 227°–228° C.

EXAMPLE 13

Analogously to Example 9, a solution of 2.0 g of 17,21-diacetoxy-4-pregnene-3,20-dione and 5.0 g of paraformaldehyde in 60 ml of methylene chloride is reacted in 2.0 g of sodium acetate and 7.6 ml of phosphorus oxychloride, and worked up, isolating is this way 1.05 g of 17,21-diacetoxy-6-methylene-4-pregnene-3,20-dione, mp 225.5°–228° C.

EXAMPLE 14

1.0 g of 17,21-diacetoxy-4-pregnene-3,20-dione is reacted analogously to Example 9 with formaldehyde diethylacetal, and worked up, thus obtaining 790 mg of 17,21-diacetoxy-6-methylene-4-pregnene-3,20-dione, mp 227°–228° C.

EXAMPLE 15

Under the conditions of Example 9, a solution of 1.0 g of 17,21-diacetoxy-4-pregnene-3,20-dione and 2.5 g of trioxane in 30 ml of methylene chloride is reacted with 1.0 g of sodium acetate and 3.8 ml of phosphorus oxychloride, and worked up, Yield: 530 mg of 17,21-diacetoxy-6-methylene-4-pregnene-3,20-dione, mp 225.5°–228° C.

EXAMPLE 16

2.0 g of 4-androstene-3,17-dione is reacted under the conditions of Example 9 to 1.41 g of 6-methylene-4-androstene-3,17-dione, mp 163°–164° C.

EXAMPLE 17

2.0 g of 4-pregnene-3,20-dione is reacted under the conditions of Example 9 to 1.84 g of 6-methylene-4-pregnene-3,20-dione, mp 131°–132° C.

EXAMPLE 18

Analogously to Example 9, 2.0 g of 21-acetoxy-4-pregnene-3,20-dione is reacted to 1.72 g of 21-acetoxy-6-methylene-4-pregnene-3,20-dione, mp 112.5°–114° C.

EXAMPLE 19

1.0 g of 17α-acetoxy-21-ethoxyacetoxy-D-homo-4-pregnene-3,20-dione is reacted analogously to Example 1 to 680 mg of 17α-acetoxy-21-ethoxyacetoxy-6-methylene-D-homo-4-pregnene-3,20-dione, mp 141.5°–143° C.

EXAMPLE 20

Under the conditions of Example 9, 2.0 g of 17β-acetoxy-17α-methyl-4-androsten-3-one is reacted to 1.58 g of 17β-acetoxy-17α-methyl-6-methylene-4-androsten-3-one, mp 142°–144° C.

EXAMPLE 21

Analogously to Example 9, 2.0 g of 17β-propionyloxy-17α-vinyl-4-androsten-3-one is reacted to 1.32 g of 6-methylene-17β-propionyloxy-17α-vinyl-4-androsten-3-one, mp 127°–130° C.

EXAMPLE 22

Analogously to Example 9, 1.0 g of 17α-(1-propionyl)-17β-propionyloxy-4-androsten-3-one is reacted to 635 mg of 6-methylene-17α-(1-propionyl)-17β-propionyloxy-4-androsten-3-one, mp 139°–140° C.

EXAMPLE 23

3.0 g of 17α-acetoxy-21-fluoro-4-pregnene-3,20-dione is reacted under the conditions of Example 9 to 2.36 g of 17α-acetoxy-21-fluoro-6-methylene-4-pregnene-3,20-dione, mp 202.5°–205° C.

EXAMPLE 24

Under the conditions of Example 9, 1.5 g of 17α-acetoxy-16-methylene-4-pregnene-3,20-dione is reacted to 910 mg of 17α-acetoxy-6,16-dimethylene-4-pregnene-3,20-dione, mp 220°–222° C.

EXAMPLE 25

2.0 g of 16α,17α-methylene-4-pregnene-3,20-dione is reacted analogously to Example 9 to 1.59 g of 6-methylene-16α,17α-methylene-4-pregnene-3,20-dione, mp 166.5°–168° C.

EXAMPLE 26

Analogously to Example 9, 2.0 g of 16α,17α-isopropylidenedioxy-4-pregnene-3,20-dione is reacted to 1.73 g of 16α,17α-isopropylidenedioxy-6-methylene-4-pregnene-3,20-dione, mp 223°–224.5° C.

EXAMPLE 27

Under the conditions of Example 9, 1.5 g of 16α,17α-epoxy-4-pregnene-3,20-dione is reacted to 863 mg of 16α,17α-epoxy-6-methylene-4-pregnene-3,20-dione, mp 185°–187° C.

EXAMPLE 28

Under the conditions of Example 9, 2.0 g of 3-oxo-4,17(20)-pregnadien-21-oic acid ethyl ester is reacted to 1.26 g of 6-methylene-3-oxo-4,17(20)-pregnadien-21-oic acid ethyl ester, mp 161.5°–162° C.

EXAMPLE 29

2.0 g of 17α,21-diacetoxy-4-pregnene-3,11,20-trione is reacted analogously to Example 9 to 1.76 g of 17α,21-diacetoxy-6-methylene-4-pregnene-3,11,20-trione, mp 228°–230° C.

EXAMPLE 30

Analogously to Example 9, 2.0 g of 17α,20;20,21-bis-methylenedioxy-4-pregnene-3,11-dione is reacted to 1.54 g of 6-methylene-17α,20;20,21-bismethylenedioxy-4-pregnene-3,11-dione, mp 198.5°–201° C.

EXAMPLE 31

1.0 of 17α,21-diacetoxy-4,9(11)-pregnadiene-3,20-dione is reacted analogously to Example 1 to 723 mg of 17α,21-diacetoxy-6-methylene-4,9(11)-pregnadiene-3,20-dione, mp 208.5°–211° C.

EXAMPLE 32

Under the conditions of Example 9, 2.0 g of 21-acetoxy-4,9(11),16-pregnatriene-3,20-dione is reacted to 1.15 g of 21-acetoxy-6-methylene-4,9(11),16-pregnatriene-3,20-dione, mp 155°–157° C.

EXAMPLE 33

Analogously to Example 9, 1.0 g of 21-acetoxy-17α-methoxy-4-pregnene-3,20-dione is reacted, yielding 0.58 g of 21-acetoxy-17α-methoxy-6-methylene-4-pregnene-3,20-dione, mp 141.5°–143° C.

EXAMPLE 34

Analogously to Example 9, 0.5 g of 17α-hexanoyloxy-19-methoxy-4-pregnene-3,20-dione is reacted to 0.31 g of 17α-hexanoyloxy-19-methoxy-6-methylene-4-pregnene-3,20-dione, mp 94°–96° C.

EXAMPLE 35

A suspension of 1.0 g of sodium acetate in 30 ml of chloroform, 30 ml of formaldehyde diethylacetal, and 3.8 ml of phosphorus oxychloride is agitated in a two-necked flask for 1 hour at a bath temperature of 65° C. and then combined with 1.0 g of 17α-hydroxyprogesterone. The mixture is stirred for 1.5 hours at 65° C., cooled to room temperature, and under vigorous agitation a saturated soda solution is added dropwise until alkaline reaction occurs. The organic phase is separated, washed neutral with water, dried over sodium sulfate, and concentrated under vacuum. The crude product is purified on 220 g of silica gel with a methylene chloride/acetone gradient (0–12% acetone), thus obtaining 842 mg of 17α-hydroxy-6-methylene-4-pregnene-3,20-dione, mp 218°–220° C.

EXAMPLE 36

Analogously to Example 35, 1.0 g of 21-acetoxy-17α-hydroxy-4-pregnene-3,20-dione is stirred with a suspension of 1.0 g of sodium acetate in 30 ml of chloroform, 30 ml of formaldehyde diethylacetal, and 3.8 ml of phosphorus oxychloride for 7 hours at 65° C., and then worked up. The crude product is purified on 220 g of silica gel with a methylene chloride/acetone gradient (0–12% acetone), thus obtaining 890 mg of 21-acetoxy-17α-hydroxy-6-methylene-4-pregnene-3,20-dione, mp 194.5°–196° C.

EXAMPLE 37

1.0 g of 21-acetoxy-17α-hydroxy-D-homo-4-pregnene-3,20-dione is reacted analogously to Example 35 to 790 mg of 21-acetoxy-17α-hydroxy-6-methylene-D-homo-4-pregnene-3,20-dione, mp 187°–188° C.

EXAMPLE 38

In a two-necked flask, a suspension of 1.0 g of sodium acetate, 1.0 g of 21-acetoxy-17α-hydroxy-4,9-pregnadiene-3,20-dione in 30 ml of chloroform, 30 ml of formaldehyde diethylacetal, and 3.8 ml of phosphorus oxychloride is stirred for 1 hour at a bath temperature of 65° C. The mixture is cooled to room temperature and, under vigorous agitation, a saturated soda solution is added dropwise until an alkaline reaction is obtained. The organic phase is separated, washed neutral with water, dried over sodium sulfate, and concentrated under vacuum. The crude product is purified on 200 g of silica gel with a hexane/ethyl acetate gradient (0–50% ethyl acetate), yielding 742 mg of 21-acetoxy-17α-hydroxy-6-methylene-4,9-pregnadiene-3,20-dione, mp 191°–193° C.

EXAMPLE 39

Analogously to Example 38, 1.0 g of 17β-hydroxy-17α-methyl-4-androsten-3-one is reacted with a suspension of 1.0 g of sodium acetate in 30 ml of chloroform, 30 ml of formaldehyde diethylacetal, and 3.8 ml of phosphorus oxychloride, and worked up. Yield: 590 mg of 17β-hydroxy-17α-methyl-6-methylene-4-androsten-3-one, mp 147.5°–150° C.

EXAMPLE 40

Under the conditions of Example 38, 2.0 g of 17α-ethynyl-17β-hydroxy-4-androsten-3-one is reacted to 1.45 g of 17α-ethynyl-17β-hydroxy-6-methylene-4-androsten-3-one, and worked up, mp 243°–245° C.

EXAMPLE 41

A suspension of 1.0 g of sodium acetate in 30 ml of chloroform and 30 ml of methylal is combined with 1.9 ml of phosphorus oxychloride and refluxed for 1 hour. The reaction mixture is combined with 1.0 g of 17β-acetoxy-17α-ethynyl-4-androsten-3-one and, under reflux, 1.9 ml of phosphorus oxychloride is added dropwise within 2 hours. The mixture is refluxed for 1 hour, cooled, and rendered alkaline by the dropwise addition of saturated soda solution. The organic phase is separated and concentrated under vacuum. For working-up purposes, the crude product is mixed with a small amount of methylene chloride and water, as well as 5 g of soda. After steam distillation, the product is vacuum-filtered, the residue washed neutral with water, and purified on 105 g of silica gel with a hexane/ethyl acetate gradient (0–50% ethyl acetate). In this way, 630 mg of 17β-acetoxy-17α-ethynyl-6-methylene-4-androsten-3-one is isolated, mp 158°–160° C.

EXAMPLE 42

A suspension of 1.0 g of sodium acetate in 30 ml of chloroform, 30 ml of formaldehyde diethylacetal, and 3.8 ml of phosphorus oxychloride is combined with 1.0 g of 5-androstene-7,17-dione and refluxed for 6½ hours. Under agitation, a saturated soda solution is then added dropwise until alkaline reaction occurs in the aqueous phase. The organic phase is separated, washed with water, dried over sodium sulfate, and concentrated under vacuum. The crude product is purified on 200 g of silica gel with a hexane/ethyl acetate gradient (0–50% ethyl acetate), thus isolating 840 mg of 4-methylene-5-androstene-7,17-dione, mp 131.5°–132° C.

EXAMPLE 43

Analogously to Example 42, 1.0 g of 21-acetoxy-17aα-hydroxy-D-homo-4-pregnene-3,20-dione is reacted, worked up, and purified, thus obtaining 640 mg of 21-acetoxy-17aα-hydroxy-6-methylene-D-homo-4-pregnene-3,20-dione, mp 187°–189° C.

EXAMPLE 44

1.0 g of D-homo-4,17-pregnadiene-3,20-dione is reacted and purified under the conditions of Example 42, thus isolating 530 mg of 6-methylene-D-homo-4,17-pregnadiene-3,20-dione, mp 138°–139° C.

EXAMPLE 45

Under the conditions of Example 42, 2.0 g of 21-acetoxy-9α-fluoro-17-hydroxy-11β-trifluoroacetoxy-4-pregnene-3,20-dione is reacted to 1.1 g of 21-acetoxy-9α-fluoro-17-hydroxy-6-methylene-11β-trifluoroacetoxy-4-pregnene-3,20-dione and worked up, mp 116.5°–117° C.

EXAMPLE 46

0.5 g of 21-acetoxy-14α,17α-dihydroxy-4-pregnene-3,20-dione is reacted and purified analogously to Example 1 yielding 0.18 g of 21-acetoxy-6-methylene-14α,17-methylenedioxy-4-pregnene-3,20-dione, mp 171°–174° C.

EXAMPLE 47

Analogously to Example 42, 3.0 g of 21.acetoxy-17α-hydroxy-11β-trimethylsilyloxy-4-pregnene-3,20-dione is reacted to 670 mg of 21-acetoxy-11β,17α-dihydroxy-6-methylene-4-pregnene-3,20-dione and purified, mp 203°–205° C.

EXAMPLE 48

Analogously to Example 42, 1.0 g of 21-chloro-16α,17-isopropylidenedioxy-4,9(11)-pregnadiene-3,20-dione is reacted and purified, thus obtaining 230 mg of 21-chloro-16α,17-isopropylidenedioxy-6-methylene-4,9(11)-pregnadiene-3,20-dione, mp 239°–242° C.

EXAMPLE 49

Analogously to Example 42, 1.0 g of 17α-acetoxy-4-pregnene-3,20-dione is reacted with 3.8 ml of ethyldichlorophosphate and worked up, thus obtaining 510 mg of 17α-acetoxy-6-methylene-4-pregnene-3,20-dione, mp 231°–233° C.

EXAMPLE 50

1.0 g of 21-acetoxy-17α-hydroxy-4-pregnene-3,20-dione is reacted, using 2.0 g of p-toluenesulfonic acid, analogously to Example 42 and purified, thus obtaining 680 mg of 21-acetoxy-17α-hydroxy-6-methylene-4-pregnene-3,20-dione, mp 194°–196° C.

EXAMPLE 51

Analogously to Example 42, using 0.2 ml of concentrated sulfuric acid, 1.0 g of 17α-acetoxy-4-pregnene-3,20-dione yields 490 mg of 17α-acetoxy-6-methylene-4-pregnene-3,20-dione, mp 234°–236° C.

EXAMPLE 52

1.0 g of 17-acetoxy-4-pregnene-3,20-dione is reacted and worked up analogously to Example 42 with 20 ml of concentrated hydrochloric acid, yielding 410 mg of 17-acetoxy-6-methylene-4-pregnene-3,20-dione, mp 230°–234° C.

EXAMPLE 53

Under the conditions of Example 42, using 15 g of a strongly acidic cation exchanger on polyacrylate basis, 1.0 g of 17-acetoxy-4-pregnene-3,20-dione yields 320 mg of 17-acetoxy-6-methylene-4-pregnene-3,20-dione after working up of the reaction mixture, mp 236°–238° C.

EXAMPLE 54

Under the conditions of Example 42, 35 ml of formaldehyde diisopropylacetal is used to react 1.0 g of $17\alpha$-acetoxy-4-pregnene-3,20-dione, yielding, after a working-up step, 480 mg of $17\alpha$-acetoxy-6-methylene-4-pregnene-3,20-dione, mp 233.5°–235° C.

EXAMPLE 55

Analogously to Example 42, 1.0 g of $17\alpha$-acetoxy-4-pregnene-3,20-dione yields, with the use of 0.2 ml of 70% perchloric acid, 450 mg of $17\alpha$-acetoxy-6-methylene-4-pregnene-3,20-dione, mp 234°–236.5° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for preparing a 6-methylene-$\Delta^4$-3-keto steroid of the formula

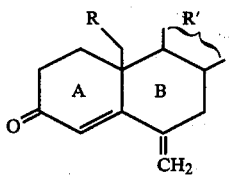

wherein

R is hydrogen, alkoxy of up to 6 carbon atoms or acyloxy of up to 6 carbon atoms wherein the acyl group is that of a carboxylic acid, and R' is the CD-ring system of a steroid of the androstane or pregnane series, comprising reacting the corresponding $\Delta^4$-3-keto steroid of the formula

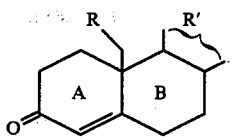

with a formaldehyde derivative of the formula

$X(CH_2O)_nY$ wherein n is 1, 3 or an integer on the order of 100–1000, and

X is $C_{1-5}$ alkoxy and Y is $C_{1-5}$ alkyl when n is 1,

X and Y represent a single bond between the terminal C atom and the terminal O atom when n is 3, and X is hydroxy and Y is hydrogen when n is an integer on the order of 100–1000, in an inert solvent, in the presence of a strong, acidic condensation agent.

2. A process of claim 1 wherein the formaldehyde derivative is $H_2C(OX)_2$ wherein X is methyl, ethyl or isopropyl.

3. A process of claim 1 wherein the formaldehyde derivative is trioxane.

4. A process of claim 1 wherein the condensation agent is phosphorus pentoxide or phosphorous oxychloride.

5. A process of claim 4 wherein the condensation agent is phosphorus pentoxide on a support material.

6. A process of claim 4 wherein the condensation agent is phosphorus oxychloride in the presence of sodium acetate.

7. A process of claim 1, 2, or 3 wherein the CD ring is of the formula

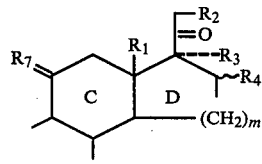

wherein m = 1 or 2, $R_1$ is methyl or ethyl, $R_2$ is hydrogen, acyloxy of up to 12 carbon atoms, halogen, alkoxy of up to 6 carbon atoms, or an acetal group of the formula

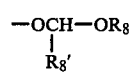

wherein $R'_8$ is hydrogen or alkyl of up to 6 carbon atoms and $R_8$ is alkyl of up to 6 carbon atoms, $R_3$ is hydrogen, hydroxy, or alkyl, alkoxy or acyloxy, each of up to 6 carbon atoms, nitrooxy, or an acetal or hemithioacetal group of the formula

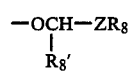

wherein $R'_8$ and $R_8$ are as defined above, and Z is oxygen or sulfur, $R_4$ is hydrogen, $\alpha$- or $\beta$-alkyl, alkylidene, $\alpha$- or $\beta$-acyloxy, $\alpha$- or $\beta$-alkoxy, each of up to 6 carbon atoms or $\alpha$- or $\beta$-$OCH_2OR_8$ wherein $R_8$ is as defined above, or $R_3$ and $R_4$ together represent oxygen, methylene, or the group

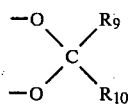

wherein R₉ and R₁₀ can be identical or different and each is hydrogen, alkyl, or alkoxy, each of up to 6 carbon atoms, and R₇ is oxygen; or hydrogen and trimethylsilyl, β-hydroxy, nitrooxy, β-halogen such as fluorine or chlorine, lower α- or β- acyloxy, lower α- or β-alkoxy, each of up to 6 carbon atoms, α- or β-methoxymethoxy; or methylene; or

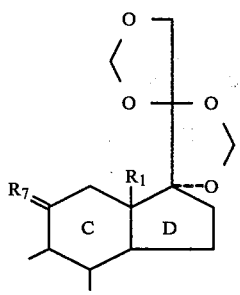

wherein R₁ and R₇ are as defined above; or

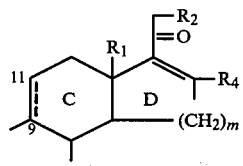

wherein m, R₁, R₂ and R₄ are as defined above, and C$\overline{9}$-C₁₁ is a CC single or double bond; or

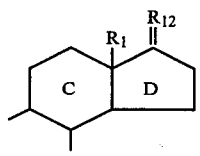

wherein R₁ is as defined above and R₁₂ is oxygen, ethylenedioxy, or =C—COOR₈ wherein R₈ is as defined above; or

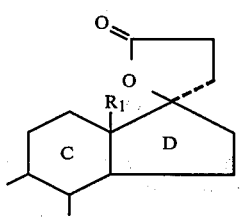

wherein R₁ is as defined above; or

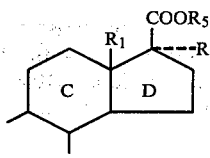

wherein R₁ and R₃ are as defined above and R₅ is alkyl or haloalkyl, each of up to 6 carbon atoms; or

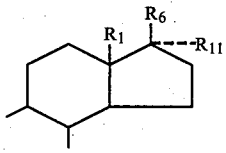

wherein
R₁ is as defined above and
R₆ is hydroxy, acyloxy of up to 6 carbon atoms, nitrooxy, alkoxy of up to 6 carbon atoms, or the acetal or hemithioacetal group of the formula

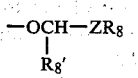

wherein
R₈, R'₈ and Z are as defined above, and
R₁₁ is alkyl, alkenyl or alkynyl, each of up to 6 carbon atoms, which can optionally be substituted by fluorine, chlorine or bromine, or

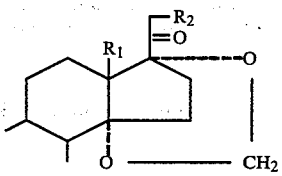

wherein R₁ and R₂ are as defined above.

8. A process of claim 1 wherein the temperature is 20°–80° C.

9. A process of claim 1 wherein the amount of reaction components are as follows:
condensation agent: 0.5–10 molar equivalents per mole of starting steroid; and
formaldehyde derivative: 5–50 molar equivalents per mole of starting steroid.

10. A process of claim 1 wherein the condensation agent is a strong acid having a pKa<1 or a strongly acidic cation exchanger.

11. A process of claim 10 wherein the condensation agent is a phosphorus acid derivative which is phosphorus pentoxide, phosphorus oxychloride, phosphorus oxytribromide, ethyl dichlorophosphite or phosphorus pentachloride.

12. A process of claim 1 wherein the condensation agent is a strong acid of pKa<1.

13. A process of claim 12 wherein the condensation agent is concentrated sulfuric acid, hydrochloric acid, p-toluenesulfonic acid or perchloric acid.

* * * * *